(12) United States Patent
Green et al.

(10) Patent No.: US 11,577,279 B2
(45) Date of Patent: Feb. 14, 2023

(54) METHOD AND APPARATUS FOR SORTING HETEROGENEOUS MATERIAL

(71) Applicant: JJG IP Holdings LLC, Hampstead, NH (US)

(72) Inventors: John F. Green, Baldwinsville, NY (US); Peter A. Mendre, Haverhill, MA (US)

(73) Assignee: JJG IP Holdings LLC, Baldwinsville, NY (US)

( * ) Notice: Subject to any disclaimer, the term of this patent is extended or adjusted under 35 U.S.C. 154(b) by 461 days.

(21) Appl. No.: 16/410,246

(22) Filed: May 13, 2019

(65) Prior Publication Data

US 2019/0262866 A1 Aug. 29, 2019

Related U.S. Application Data

(63) Continuation of application No. 15/921,766, filed on Mar. 15, 2018, now Pat. No. 10,328,464, which is a
(Continued)

(51) Int. Cl.
*B07C 5/34* (2006.01)
*A61K 9/00* (2006.01)
(Continued)

(52) U.S. Cl.
CPC .............. *B07C 5/34* (2013.01); *A61K 9/0019* (2013.01); *A61K 31/498* (2013.01); *A61K 47/10* (2013.01);
(Continued)

(58) Field of Classification Search
CPC ... B07C 5/34; B07C 5/368; B07C 2501/0018; A61K 9/0019; A61K 31/498;
(Continued)

(56) References Cited

U.S. PATENT DOCUMENTS 3,802,558 A * 4/1974 Rhys ...................... B07C 5/3425
209/636
4,344,539 A * 8/1982 Lockett ................. B07C 5/3425
209/582
(Continued)

FOREIGN PATENT DOCUMENTS

WO 03061858 A1 7/2003
WO 2006054154 A1 5/2006
(Continued)

OTHER PUBLICATIONS

*Color Image Processing: Methods and Applications*, Excerpts Including Chapter 17: Spectral Imaging and Applications by Carlsohn et al., Published 2007, 61 pages.
(Continued)

*Primary Examiner* — Kyle O Logan
(74) *Attorney, Agent, or Firm* — Maine Cernota & Rardin

(57) ABSTRACT

A system is provided for the identification and separation of heterogeneous material, the system comprising: a hyperspectral identification system for capturing spectra of material; a computer receiving and analyzing data from the hyperspectral identification system and selecting desired materials from the heterogeneous materials; and an ejection system, whereby the desired materials are ejected from the system.

23 Claims, 7 Drawing Sheets

Related U.S. Application Data continuation of application No. 14/259,584, filed on Apr. 23, 2014, now Pat. No. 9,950,346, which is a continuation of application No. 12/620,909, filed on Nov. 18, 2009, now abandoned.

(60) Provisional application No. 61/115,771, filed on Nov. 18, 2008.

(51) Int. Cl.

| | | |
|---|---|---|
| *A61K 47/10* | (2017.01) | |
| *A61K 47/18* | (2017.01) | |
| *A61K 47/32* | (2006.01) | |
| *A61K 47/38* | (2006.01) | |
| *B07C 5/342* | (2006.01) | |
| *B07C 5/36* | (2006.01) | |
| *A61K 31/498* | (2006.01) | |
| *C07C 51/41* | (2006.01) | |
| *C07C 65/11* | (2006.01) | |
| *C07D 403/12* | (2006.01) | |

(52) U.S. Cl.
CPC .......... *A61K 47/183* (2013.01); *A61K 47/32* (2013.01); *A61K 47/38* (2013.01); *B07C 5/342* (2013.01); *B07C 5/368* (2013.01); *C07C 51/41* (2013.01); *C07C 65/11* (2013.01); *C07D 403/12* (2013.01); *B07C 2501/0018* (2013.01)

(58) Field of Classification Search
CPC ...... A61K 47/10; A61K 47/183; A61K 47/32; A61K 47/38; C07C 51/41; C07C 65/11; C07D 403/12
See application file for complete search history.

(56) References Cited

U.S. PATENT DOCUMENTS

| | | | |
|---|---|---|---|
| 5,134,291 A | 7/1992 | Ruhl, Jr. et al. | |
| 5,339,961 A | 8/1994 | Mayhak | |
| 5,862,919 A * | 1/1999 | Eason | B07C 5/00 209/939 |
| 6,003,681 A | 12/1999 | Wilbur et al. | |
| 6,008,492 A | 12/1999 | Slater et al. | |
| 6,143,183 A * | 11/2000 | Wardwell | B04B 1/20 210/85 |
| 6,353,197 B1 | 3/2002 | Ulrichsen et al. | |
| 6,646,264 B1 | 11/2003 | Modiano et al. | |
| 7,264,124 B2 | 9/2007 | Bohlig et al. | |
| 7,335,387 B2 | 2/2008 | Hayes et al. | |
| 9,950,346 B2 | 4/2018 | Green et al. | |
| 2004/0044436 A1 | 3/2004 | Arleth et al. | |
| 2005/0127285 A1 | 6/2005 | Kampf et al. | |
| 2006/0042527 A1 * | 3/2006 | Deppermann | G01N 35/00029 111/171 |
| 2007/0029232 A1 * | 2/2007 | Cowling | B07C 5/3425 209/577 |
| 2007/0278139 A1 * | 12/2007 | Cowling | B07C 5/36 209/606 |
| 2008/0046217 A1 * | 2/2008 | Polonskiy | G01J 3/28 702/179 |
| 2008/0257793 A1 * | 10/2008 | Valerio | B07C 5/3427 209/567 |
| 2009/0087033 A1 | 4/2009 | Chao et al. | |
| 2009/0306816 A1 * | 12/2009 | Champel | B07C 5/34 700/223 |

FOREIGN PATENT DOCUMENTS

| | | |
|---|---|---|
| WO | 2007112591 A1 | 10/2007 |
| WO | 2009094618 A | 7/2009 |

OTHER PUBLICATIONS

Declaration of Dr. Gonzalo R. Arce, Dated May 3, 2020, 86 pages.
A. Kulcke et al., *On-line classification of synthetic polymers using near infrared spectral imaging*, J. Near Infrared Spectrosc. 11 (2003), 11 pages.
Martin Kraft, *SpectroSorting—Industrial On-Line Material Classification by Near-Infrared Spectral Imaging*, 8 pages.
Petra Tatzer et al., *Industrial application for inline material sorting using hyperspectral imaging in the NIR range*, Real-Time Imaging 11 (2005), 9 pages.
Giuseppe Bonifazi and Silvia Serranti, *Imaging spectroscopy based strategies for ceramic glass contaminats removal in glass recycling*, Waste Management 26 (2006), 13 pages.
"DC Recycles" from the Government of the District of Columbia, 2 pages.
U.S. Environmental Protection Agency, *Environmental Fact Sheet: The Facts on Recycling Plastics*, (1990), 2 pages.
List of Acceptable and Non-Acceptable Items for Recycling from Waste Management, (2005), 1 page.
Excerpts of prosecution history of U.S. Pat. No. 9,950,346, 132 pages.
Environment and Plastics Industry Council (EPIC), *A Review of Optical Technology to Sort Plastics & Other Containers* (2006), 24 pages.
A. Alberdi et al., *An experimental study on abrasive waterjet cutting of CFRP/Ti6Al4V stacks for drilling operations*, Int. J. Adv. Manuf. Technol. (2016), 14 pages.
U.S. Appl. No. 61/115,771, 22 pages.
May 9, 2007 Wayback Machine Printout of Amazon.com Page (https://www.amazon.com/Color-Image-Processing-Methods-Applications/dp/084939774X) Listing *Color Image Processing: Methods and Applications for Sale*, 5 pages.
Oct. 25, 2006 Wayback Machine Printout of http://colorimageprocessing.com/books.htm Announcing Publication of *Color Image Processing: Methods and Applications*, 1 page.
Jul. 1, 2007 Wayback Machine Printouts of Pages from http://colorimageprocessing.org Announcing Publication, Describing, and Providing Links to Purchase *Color Image Processing: Methods and Applications*, 8 pages.
U.S. Appl. No. 61/023,546, 138 pages.

* cited by examiner

METHOD AND APPARATUS FOR SORTING HETEROGENEOUS MATERIAL

RELATED APPLICATIONS

This application is a continuation of U.S. application Ser. No. 15/921,766, filed on Mar. 15, 2018, which is a continuation of U.S. application Ser. No. 14/259,584, filed on Apr. 23, 2014, which is a continuation of U.S. application Ser. No. 12/620,909, filed on Nov. 18, 2009. U.S. application Ser. No. 12/620,909 claims the benefit of U.S. Provisional Application No. 61/115,771, filed Nov. 18, 2008. These applications are herein incorporated by reference in their entirety for all purposes.

FIELD OF THE INVENTION

The invention relates to methods and apparatus for sorting heterogeneous material, and more particularly, to an automatic sorting systems for the identification and separation of such material.

BACKGROUND OF THE INVENTION

Recycling of post consumer and industrial material requires that composite materials be sorted and separated according to color, composition, shape, size, or any of several criteria. Such sorting has traditionally been done manually, wherein sorters visually identify objects to be sorted, and transfer them from one conveyer belt to another running parallel to the first. This is labor intensive and expensive. Automated systems have been developed to replace this traditional hand sorting. In such systems, materials are identified by conventional optical scanner and are transferred from a first conveyer by means of a mechanical or pneumatic force to a second conveyer. Such systems typically are imprecise in their sorting, allowing materials to be mixed, which must then be resorted before pelletization. This lack of precision is due both to the optical scanning mechanism, and the imprecise mechanical and pneumatic sorting mechanism.

Known optical sorting techniques carry materials on a conveyor or vibratory deck and then rely on air jet propulsion methods and or finger push methods that lift or push desired picked materials past an outboard barrier. Unselected items typically fall off the end of the optics conveyor or shaker deck and often dropped on a conveyor below that would transport that material to another optical system where the process occurs again. The selected ejected items that have been propelled either land on another belt or vibratory conveyor and deposited in a holding bunker often with some type of post sorting to qualify the material is correctly identified. Such a system requires extensive room, both horizontally and vertically to allow for conveyers and dropping of the materials.

What is needed therefore is a means for automated sorting heterogeneous material with high degrees of precision.

SUMMARY OF THE INVENTION

One embodiment of the present invention provides a system for the identification and sorting of heterogeneous material, the system comprising: a hyperspectral identification system for capturing spectra of material, the hyperspectral identification system comprises at least one hyperspectral camera the hyperspectral camera receiving a plurality of selected spectral bands of infrared and visible light corresponding to spectral signatures of target materials to be identified if present in the heterogeneous material; the camera disposed proximate to a visible or infrared light source, the light source and the at least one hyperspectral camera are disposed on the same side of a stream of the heterogeneous material; a solid belt having first and second ends, the belt running beneath the hyperspectral identification system and upon which the heterogeneous material is conveyed from the first end to the second end, the belt traveling at a preset rate, the hyperspectral identification system being disposed over the second end of the belt; a computer receiving and analyzing data from the hyperspectral identification system and selecting materials of a first user defined category from the materials; and an ejection system disposed immediately after the second end of the belt, whereby the desired materials are separated from the heterogeneous material, the ejection system being triggered by the computer at a preset time delay equal to the distance between the camera and the ejection system divided by the rate of travel of the belt.

A further embodiment of the present invention provides such a system further comprising a conveyer to deliver the heterogeneous material to the system.

Yet another embodiment of the present invention provides such a system further comprising a receiving system, whereby the materials of a first user defined category are segregated and collected.

A yet further embodiment of the present invention provides such a system further comprising an array of lights disposed proximate to the hyperspectral identification system.

Even another embodiment of the present invention provides such a system wherein the lights have a wavelength suitable for hyperspectral imaging.

An even further embodiment of the present invention provides such a system wherein the hyperspectral identification system is configured to collect spectral and spatial information from heterogeneous material entering the system, store the spectral and spatial information as images.

Still another embodiment of the present invention provides such a system wherein the computer comprises software configured to compare the images to images stored in a library of images.

A still further embodiment of the present invention provides such a system wherein the ejection system comprises a plurality of independently controlled air nozzles disposed beneath the material, and a blower hood disposed above the material, the blower hood providing a air current whereby the selected material is blown out of a discharge port.

Yet another embodiment of the present invention provides such a system wherein the heterogeneous materials comprise waste and recyclable materials.

A yet further embodiment of the present invention provides such a system wherein the computer can select a plurality of user defined materials.

Still yet another embodiment of the present invention provides such a system wherein the ejection system comprises a mechanical ejector.

A still yet further embodiment of the present invention provides such a system wherein the ejection system comprises a fluid jet.

Still even another embodiment of the present invention provides such a system wherein the fluid jet is a water jet.

One embodiment of the present invention provides a method for sorting heterogeneous material, the method comprising: reflecting visible or infrared light from the surface of the heterogeneous material disposed on a conveyer; conveying the heterogeneous material at a predetermined rate through a hyperspectral imager; generating hyperspectral images of the heterogeneous material by receiving a plurality of selected spectral bands of infrared and visible light corresponding to spectral signatures of target materials to be identified if present in the heterogeneous material as the heterogeneous material passes on the conveyer beneath the hyperspectral imaginer; comparing the hyperspectral images of the heterogeneous material to hyperspectral images of known materials; identifying the target materials; after a preset time interval from the identifying the target material, the interval equal to the distance between the hyperspectral imager and a separating system divided by the predetermined rate, physically isolating target material from the heterogeneous material by separating the selected material from the heterogeneous material as it leaves the conveyer immediately after the hyperspectral imager.

Another embodiment of the present invention provides such a method further comprising illuminating the heterogeneous material to optimize the hyperspectral images.

A further embodiment of the present invention provides such a method wherein the hyperspectral images comprise spectral and spatial data for articles within the heterogeneous material.

Even another embodiment of the present invention provides such a method wherein the heterogeneous material comprises waste material and recyclable material in combination.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

In one embodiment of the present invention, a system is provided having a hyperspectral identification system and a positively sorted air ejector.

Figure 1:
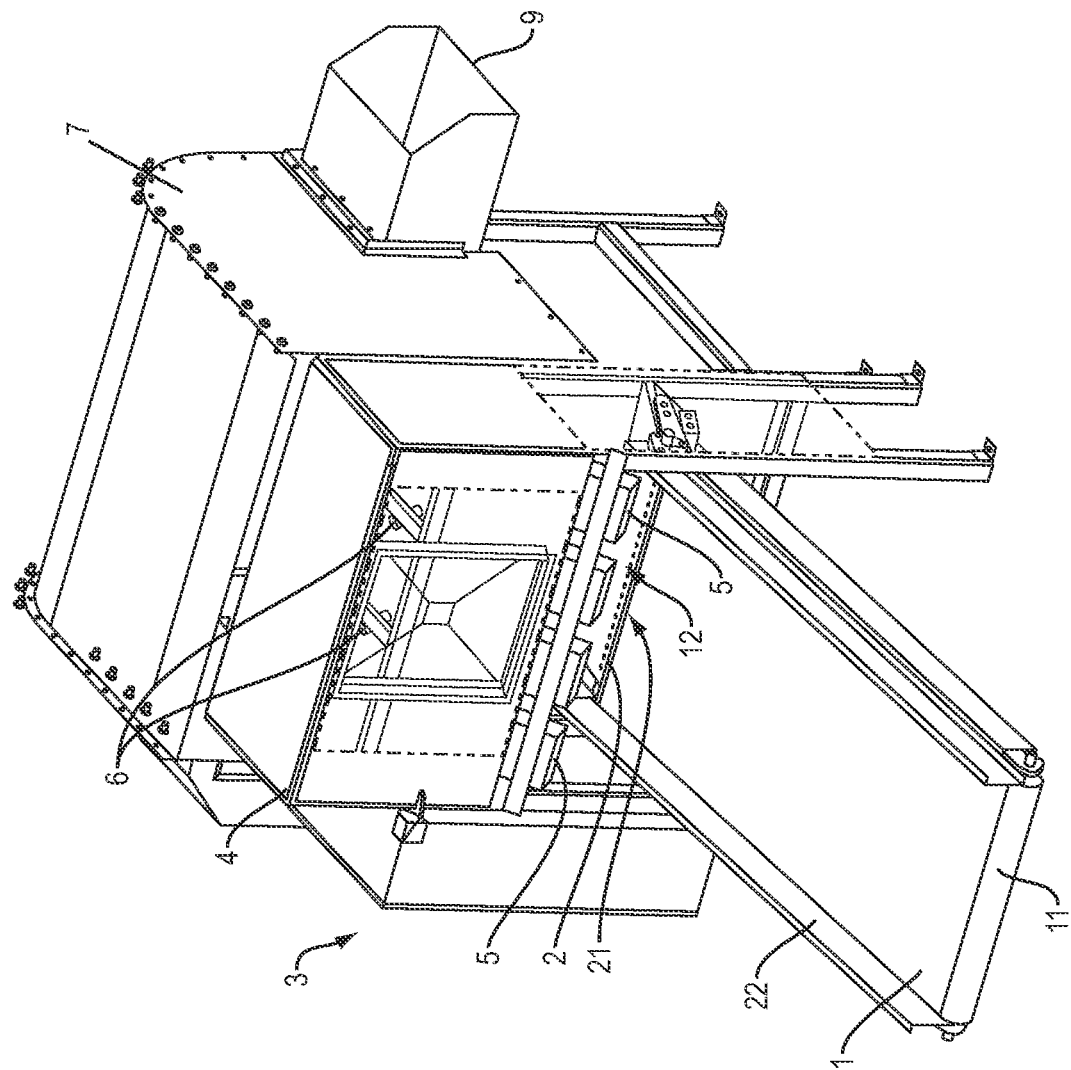
FIG. 1 is a front perspective drawing illustrating a system for the separation of heterogeneous material configured in accordance with one embodiment of the present invention.
Figure 2:
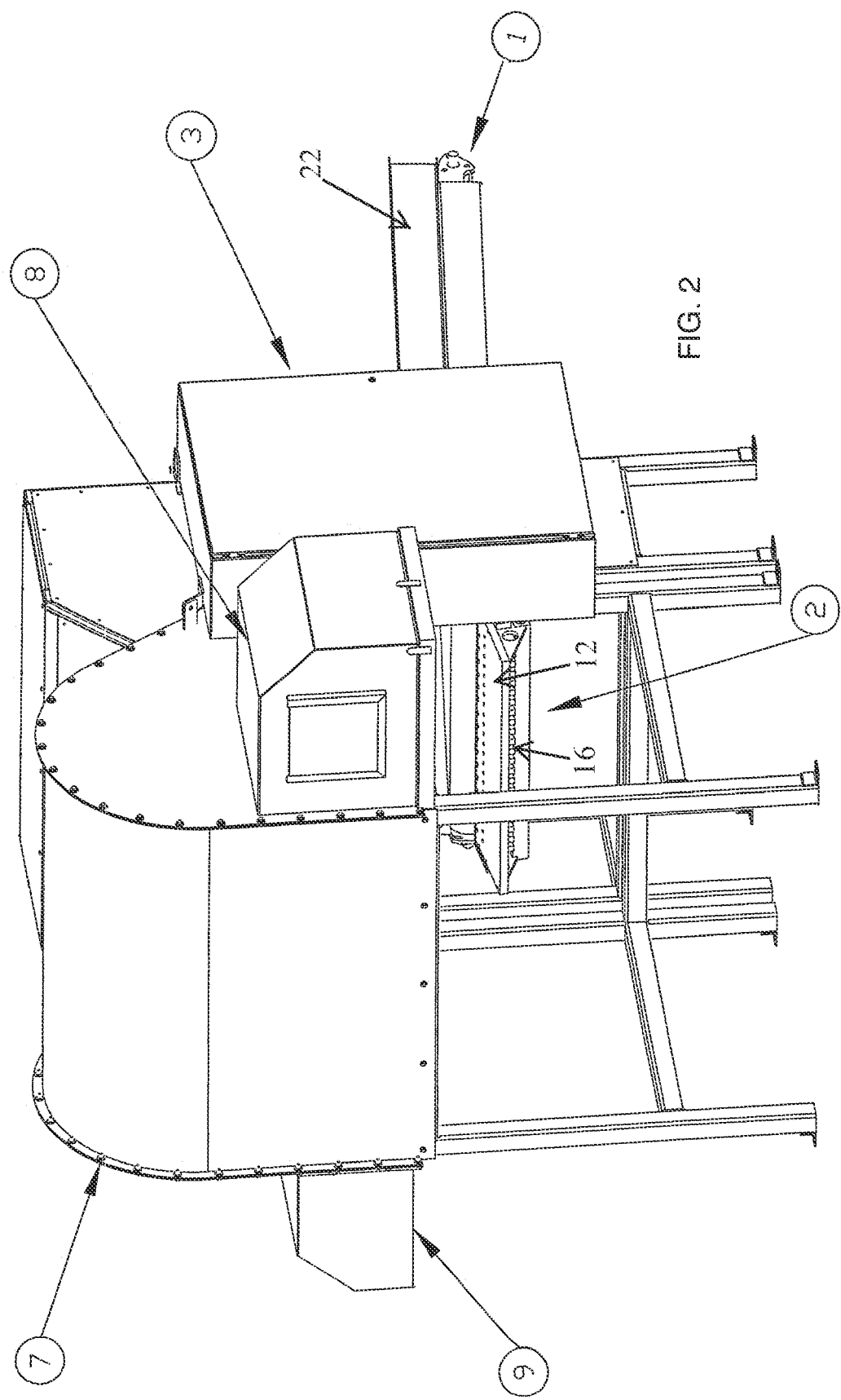
FIG. 2 is a rear perspective drawing illustrating a system for the separation of heterogeneous material configured in accordance with one embodiment of the present invention.
Figure 3:
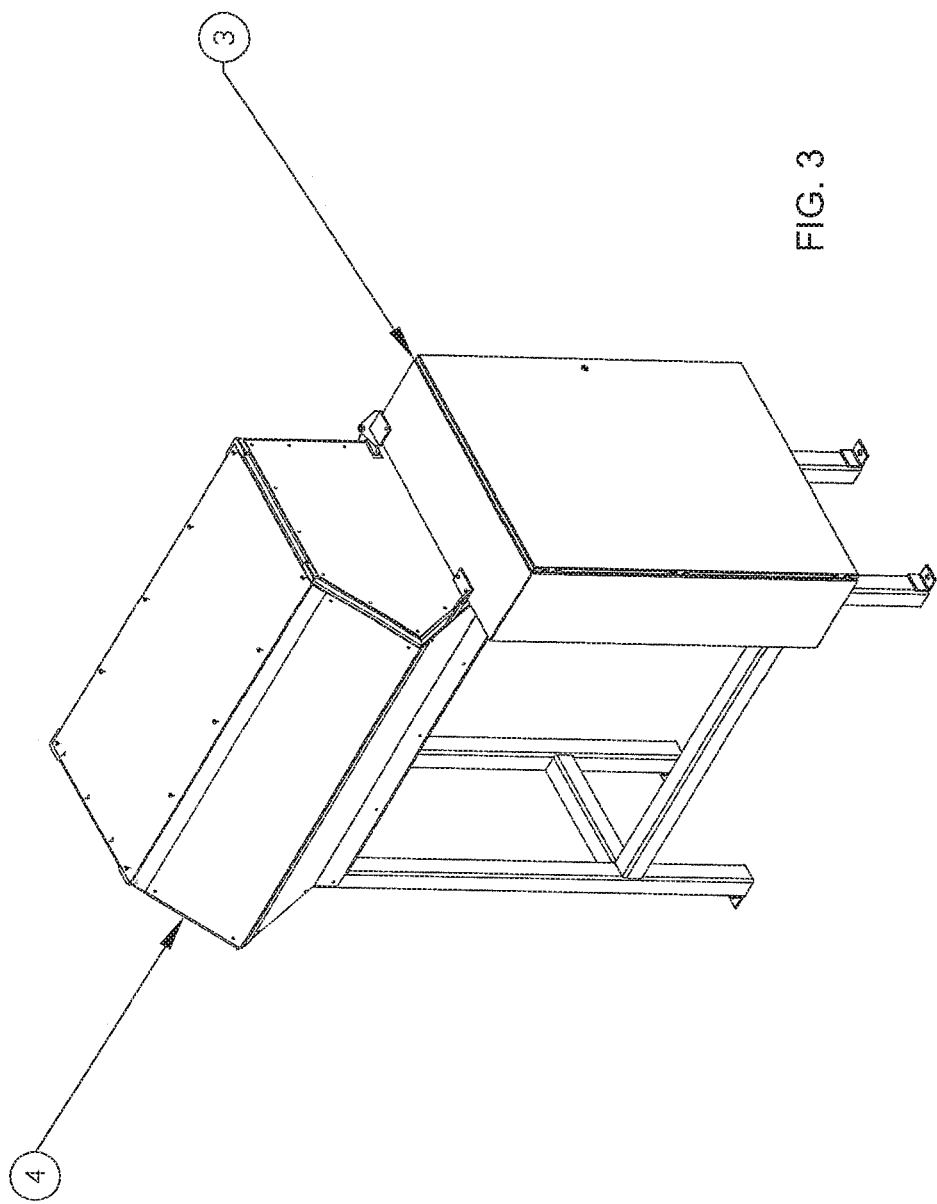
FIG. 3 is a rear perspective drawing illustrating an optical scanner of a system for the separation of heterogeneous material configured in accordance with one embodiment of the present invention.
Figure 4:
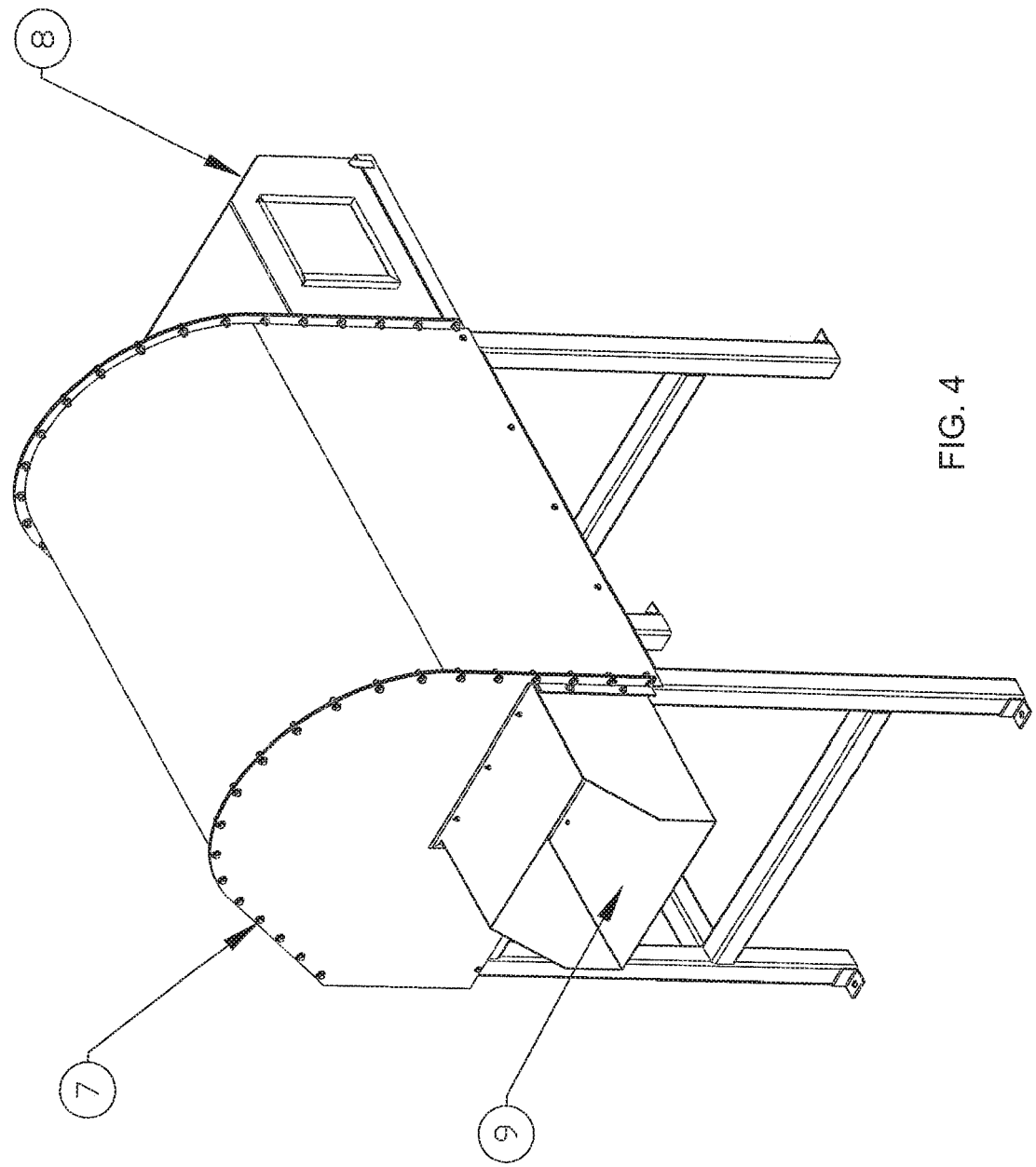
FIG. 4 is a side perspective drawing illustrating a blower hood configured for use in a system for the separation of heterogeneous material configured in accordance with one embodiment of the present invention.
Figure 5:
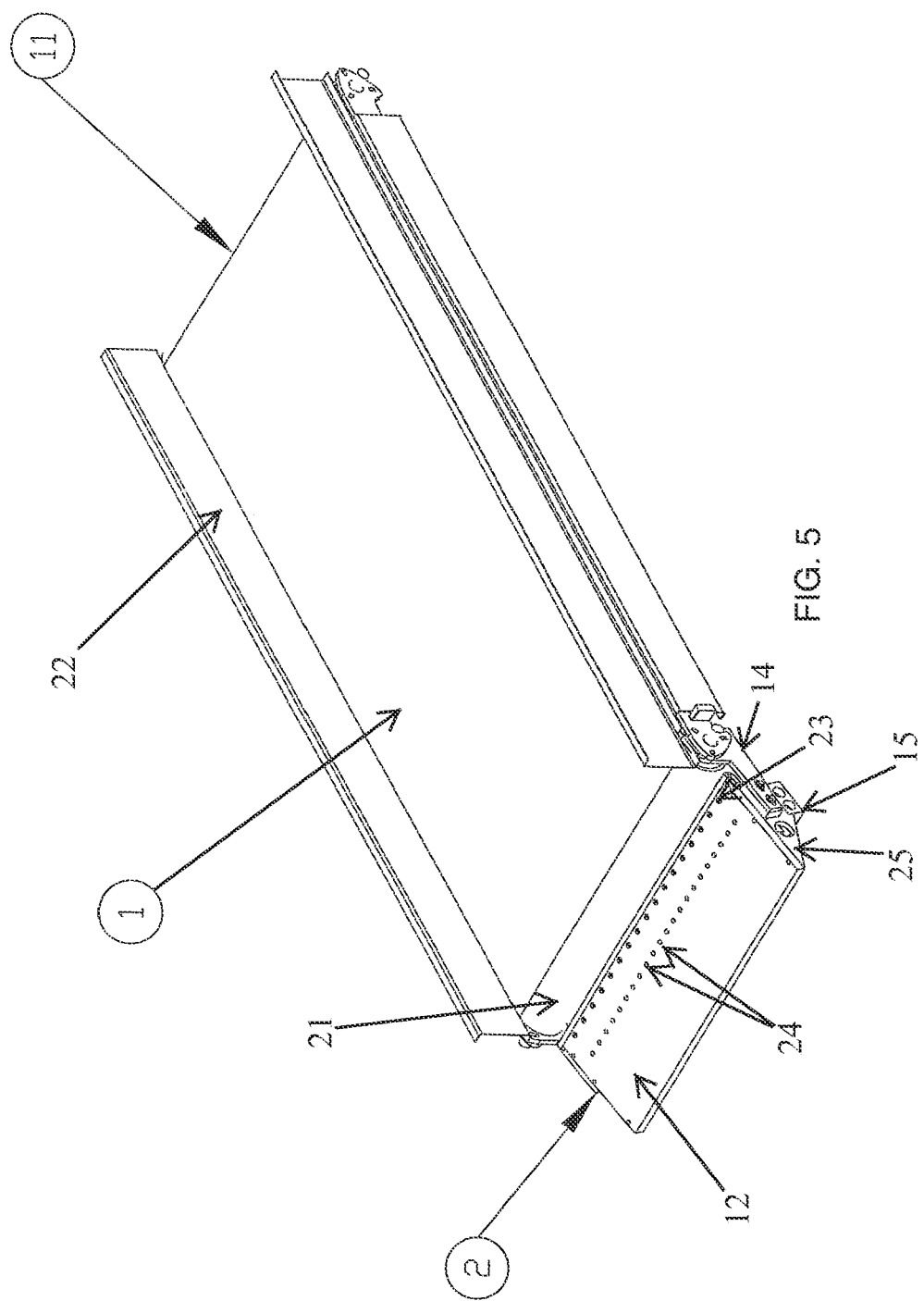
FIG. 5 is a front perspective drawing illustrating a conveyer, air knife and ejector configured for use in a system for the separation of heterogeneous material configured in accordance with one embodiment of the present invention.
Figure 6:
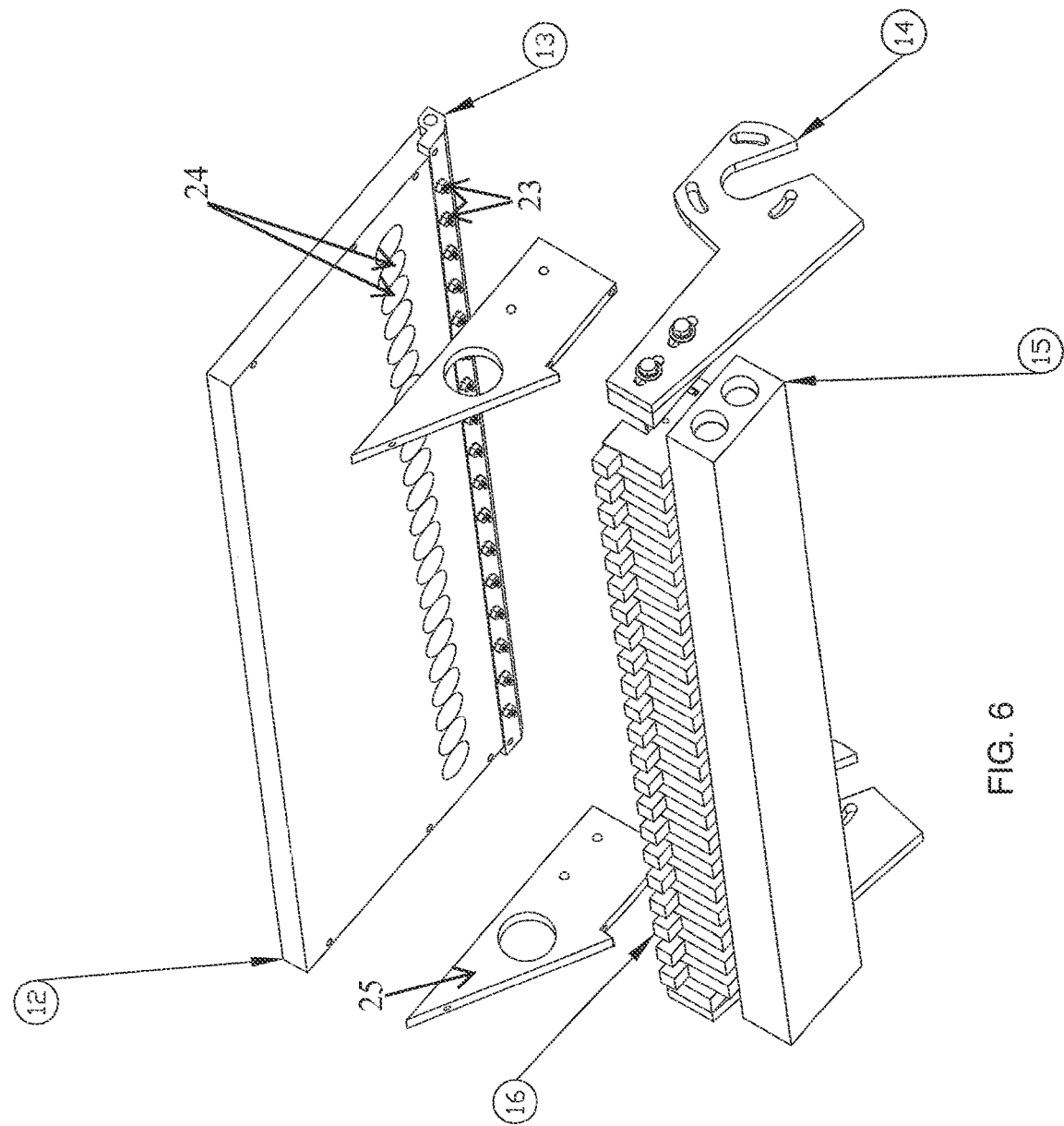
FIG. 6 is a bottom, exploded perspective drawing illustrating an air knife and ejector configured for use in a system for the separation of heterogeneous material configured in accordance with one embodiment of the present invention.
Figure 7:
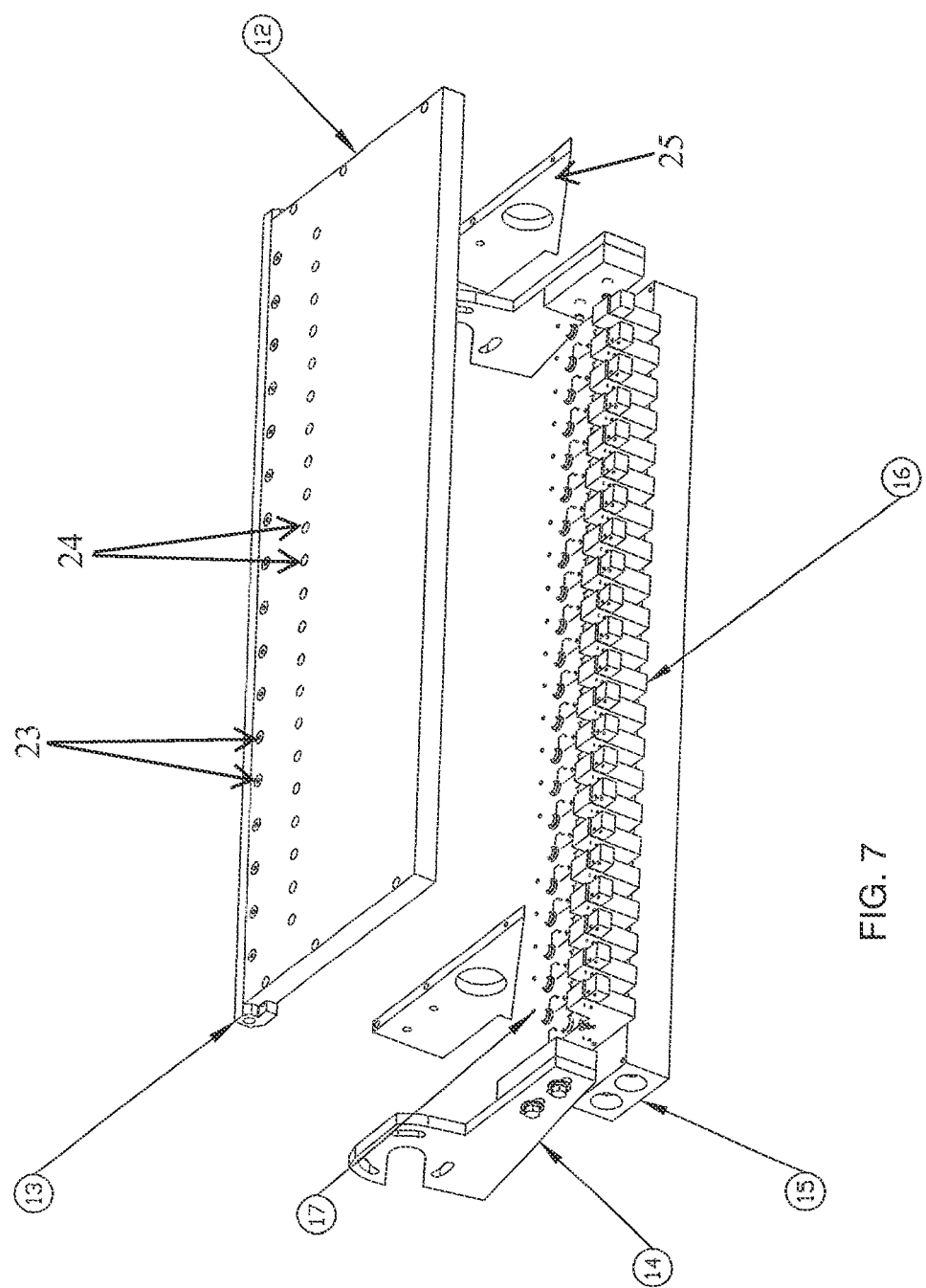
FIG. 7 is a top, exploded perspective drawing illustrating an air knife and ejector configured for use in a system for the separation of heterogeneous material configured in accordance with one embodiment of the present invention.

In one embodiment, such as that illustrated in FIGS. 1 and 2, a conveyer 1 carries material to an identification camera enclosure 4. The conveyor 1 has a first end 11 and a second end 21 proximate an air knife 2. The identification camera enclosure 4 encloses a camera 6 disposed proximately to an array of lights 5, highlighting the target area for the camera 6. In such a system, the camera 6 is a hyperspectral camera. Hyperspectral cameras and sensors such as those employed in the one embodiment of the present invention collect and then combine spatial and spectral information as a set of 'images'. In one embodiment, illustrated in FIG. 3, the camera 6 may be mounted on camera mounting brackets 10.

Each image, thus generated, represents a range of the electromagnetic spectrum and is also known as a spectral band. These 'images' are then combined and form a three dimensional hyperspectral cube for processing and analysis.

Hyperspectral sensors also referred to as "imaging spectroscopy" look at objects using a vast portion of the electromagnetic spectrum. Certain objects leave unique 'fingerprints' across the electromagnetic spectrum. These 'fingerprints' are known as spectral signatures and enable identification of the materials that make up a scanned object. Identification systems, can compare the spectral "fingerprint" of a sample with an unknown composition to a known spectra from a library of known exemplars.

Hyperspectral cameras of one embodiment of the present invention, utilize visible light, ultraviolet, and infrared spectral imaging that utilizes spatial information provided by the hyperspectral image. Infrared is, in such an embodiment, the primary band utilized in identifying individual recyclable commodities encompassing sometimes a variety of spectral signatures including color for sorting and commodity segregation purposes. One skilled in the art will appreciate that embodiments of the present invention may be used in sorting heterogeneous materials in other fields including but not limited to agriculture, medicine, and industrial applications.

Hyperspectral data, collected by the camera 6, comprises a set of contiguous bands. In one embodiment of the present invention, this is collected by a single sensor, interfaced with an ejection method that resides within its field of vision and then used to select the desired item. This is in contrast to conventional multispectral techniques, where a set of optimally chosen spectral bands that are typically not contiguous and need to be collected from multiple sensors. This collection of spectral data is valuable in improving the accuracy of the identification, and is employed in various embodiments of the present invention. A single sensor, in one embodiment of the present invention, performs all the following tasks: Identify items searched for in a large area; searching for multiple items at the same time; identifying items by composition and color all with a higher degree of positive identification. Thus a single system may be programmed to sort all commodities required by a user.

One embodiment of the present invention provides a system equipped with Wedge Jet style high flow ejection air nozzles 17 and high speed real time computer interfaces thus providing an ejection method capable of propelling desired items into an elevated air conveyance system enabling multiple units to be orientated on a straight line.

A straight line orientation enables optical sorting systems to be installed in a smaller area with no vertical grade differential, thus enabling the simple retrofit of existing manual sorting lines with optical automatic sorters with minimal site work. Such an embodiment also enables new systems to be engineered into a much smaller footprint than existing traditional saw tooth designs which require elevation consideration. A system design configured according to one embodiment of the present invention and illustrated in FIGS. 1 and 2 provides an accelerator rubber belt feed conveyor 1 of varying widths traveling at a rate of between 200 to 600 feet per minute. A guard rail 22 is positioned on each longitudinal side of conveyor 1 in some embodiments. A light bar system 5 shines a high intensity light down on the belt where the hyperspectral imaging camera 6 collects its data. The camera 6 collects that data and feeds a high speed Lenox computer system or other suitable computer system 3 that has been programmed to receive this data and then provide output signals timed with the ejector nozzles 17 to eject desired product. Immediately after the discharge of the accelerator conveyor 1 is disposed an air knife 2 that helps to levitate materials and decreases the likelihood of material lodging between the accelerator belt 1 and manifold ejector plate 12. The manifold ejection plate 12 houses the wedge jets 17 and enables those jets 17 to be directed to optimal lift. The ejection plate 12 includes a plurality of apertures 24 and a plurality of screws 23. The ejection plate 12 also includes an ejection plate bracket 13. The ejector system further includes one or more manifold ejector plate to conveyor mounting brackets 14, a manifold 15, a plurality of wedge jet connectors 16, and one or more ejection plate supports 25. The wedge jets 17, which may be also referred to as vortex, Typhoon, Hurricane or Fixed Flow Air Nozzles are fast acting, resistant to plugging and deliver a high velocity directed air flow that then expands to an 8" diameter air flow. A Venturi effect delivered by this style ejection jet positively holds the ejected item within its an flow decreasing the likelihood of the item colliding with competitive items in the air and discouraging turbulence. The additional force generated by these jets 17 propels the picked items into a receiving hood 7 area located above the accelerator belt 1. This receiving hood system 7 is fitted with a high velocity fan type blower 8 that then pushes the selected items toward the collection point 9 at a 90 degree angle. In an alternative embodiment, the ejection system can be configured with at least one flipping lever or other mechanical device whereby desired material is pushed or otherwise segregated. Negative materials not selected continue down the ejector plate 12 and are deposited on another accelerator conveyor (not shown) upon which non-selected materials move in series to additional optical system where another desired item can be sorted and removed from the waste stream. In such an embodiment, each optical sorter may be deployed in line with the previous sorter in a very tight configuration with no change in elevation. The evacuation fan within the collection hood also develops a venture effect that helps to draw light fractional items into its air stream enhancing the collection rate of ejected selected items. An evacuation conveyor could also be positioned in this location and would deliver similar results.

A further embodiment provides an accelerator conveyor enabling the spreading out of materials, a hyperspectral imaging camera designed to positively identify about approximately 100% of the desired item (for example, a recyclable material or other component of a heterogeneous material), items, air nozzle cannons with fast acting solenoid air valves which react to information provided by imaging camera designed to lift desired fractional recyclable material.

Yet another embodiment provides an air conveyance system which develops a Venturi effect drawing in the previously lifted desired items and evacuating those items to a holding bin.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:
1. A system comprising:
a conveyor belt having a first portion, a second portion, a middle portion therebetween, and a longitudinal axis extending from the first portion to the second portion, wherein the middle portion is larger than the first and second portions, the conveyor belt further comprising an upper surface and being configured to convey a heterogeneous material stream at a preset rate of travel on the upper surface and from the first portion to the second portion;
a hyperspectral identification system capable of receiving spectral and spatial data corresponding to a target recyclable material found within the heterogenous material stream, the hyperspectral identification system comprising:
a single hyperspectral camera disposed proximate to a light source and capable of receiving a plurality of spectral bands of light corresponding to spectral signatures of recyclable materials, wherein the recyclable materials include glass, paper, PET plastics, and black plastics, wherein the target recyclable material is one of the recyclable materials, the single hyperspectral camera configured to receive two or more spectral bands of light corresponding to spectral signatures of the target recyclable material and spatial data corresponding to the target recyclable material's position on the conveyor belt, wherein the hyperspectral camera is positioned above the upper surface and directly above the second portion of the conveyor belt;
a computer configured to receive from the hyperspectral identification system information corresponding to the spectral signatures of the target recyclable material and spatial data corresponding to the target recyclable material's position on the conveyor belt, using at least one of that information and data to identify the position of the target recyclable material on the conveyor belt; and
an ejector positioned immediately after the second portion of the conveyor belt and in operative communication with the computer, the ejector comprising:
a plurality of jets in one or more rows positioned substantially perpendicular to the longitudinal axis of the conveyor belt and configured to receive one or more signals from the computer to trigger one or more of the jets to move the target recyclable material, wherein the one or more signals correspond to a time delay equal to a distance along the longitudinal axis between a point at which the target recyclable material is identified by the hyperspectral identification system and the one or more jets, divided by a preset rate of travel of the conveyor belt.

2. The system according to claim 1, wherein the target recyclable material is PET plastic.

3. The system according to claim 1, further comprising a receiving system comprising a collection point, the receiving system being configured to route separated target recyclable material to the collection point for collection.

4. The system according to claim 3, wherein the receiving system comprises a receiving hood positioned above the conveyor belt and proximate the ejector, wherein the receiving hood is configured to receive target recyclable material ejected by the ejector and push the target recyclable material to the collection point.

5. The system according to claim 4, wherein the receiving system further comprises a blower configured to provide a current of air configured to move the separated target recyclable material to the collection point.

6. The system according to claim 1, wherein the light source has a wavelength suitable for hyperspectral imaging of the target recyclable material.

7. The system according to claim 1, wherein the hyperspectral identification system is configured to collect spectral and spatial information from recyclable material in the heterogeneous material stream entering the system and store the spectral and spatial information as stored images.

8. The system according to claim 1, wherein the ejector further comprises an ejection plate, and wherein each jet in the plurality of jets comprises an independently controlled ejector nozzle disposed beneath the ejection plate.

9. The system according to claim 1, wherein the heterogeneous materials stream comprises a mixture of waste and recyclable materials.

10. The system according to claim 1, wherein the target recyclable material is glass.

11. The system according to claim 1, wherein the target recyclable material is paper.

12. The system according to claim 1, wherein the single hyperspectral camera is configured to receive the two or more spectral bands of light in the visible light spectrum with wavelengths between at least 400 nm and 750 nm and configured to receive the two or more spectral bands of light in the near infrared light spectrum with wavelengths between at least 800 nm and 1700 nm.

13. The system according to claim 1, wherein the single hyperspectral camera is configured to receive two or more spectral bands of light in the visible light spectrum with wavelengths below 750 nm and configured to receive two or more spectral bands of light in the near infrared light spectrum with wavelengths up to at least 2500 nm.

14. The system according to claim 1, wherein the two or more spectral bands of light corresponding to spectral signatures of the target recyclable material are in the visible light spectrum with wavelengths below 750 nm, and the single hyperspectral camera is configured to receive two or more additional spectral bands of light corresponding to additional spectral signatures of the target recyclable material which are in the near infrared light spectrum with wavelengths up to at least 1700 nm.

15. A system for the identification and sorting of material, the system comprising:
  a solid conveyor belt having a first end opposite a second end, a first portion comprising the first end, a second portion comprising the second end, a middle portion between the first and second portions, and a longitudinal axis extending from the first end to the second end, the solid conveyor belt having an upper surface and being configured to convey a heterogeneous material stream at a preset rate of travel on the upper surface from the first portion to the second portion, wherein the heterogeneous material stream comprises a mixture of waste and recyclable materials;
  a means for receiving spectral and spatial data corresponding to a target recyclable material found within the heterogenous material stream comprising:
    a single hyperspectral camera disposed near a light source and capable of receiving a plurality of spectral bands of light corresponding to spectral signatures of desired recyclable materials, wherein the desired recyclable materials include glass, paper, PET plastics, and black plastics, wherein the target recyclable material is one of the desired recyclable materials, the single hyperspectral camera configured to receive a plurality of spectral bands of infrared and/or visible light corresponding to spectral signatures of the target recyclable material and configured to receive spatial data corresponding to the target recyclable material's position on the solid conveyor belt, wherein the single hyperspectral camera is positioned directly over the second portion and above the upper surface of the conveyor belt;
  a computer configured to receive from the means for receiving spectral and spatial data information corresponding to the spectral signatures of the target recyclable material and spatial data corresponding to the target recyclable material's position on the solid conveyor belt, wherein the computer is configured to use at least one of that information and data to identify the position of the target recyclable material on the solid conveyor belt; and
  an ejecting means positioned immediately after the second end of the solid conveyor belt and in operative communication with the computer, the ejecting means comprising:
    a plurality of independently controlled nozzles disposed after the second end of the solid conveyor belt and positioned substantially perpendicular to the longitudinal axis of the solid conveyor belt, wherein each nozzle in the plurality of independently controlled nozzles is configured to receive one or more signals from the computer to trigger one or more of the nozzles to move the target recyclable material toward a collection point that is separate from the heterogeneous material stream, wherein the one or more signals correspond to a time delay equal to a distance along the longitudinal axis between a point at which the target recyclable material is identified by the single hyperspectral camera and the one or more nozzles, divided by the preset rate of travel of the solid conveyor belt.

16. The system according to claim 15, wherein the target recyclable material is PET plastic.

17. The system according to claim 15, wherein the light source has a wavelength suitable for hyperspectral imaging the target recyclable material.

18. The system according to claim 15, wherein the plurality of spectral bands of infrared or/and visible light have wavelengths between at least 400 nm and 1700 nm.

19. The system according to claim 15, wherein the single hyperspectral camera is configured to receive the plurality of spectral bands of infrared and/or visible light with wavelengths up to at least 1700 nm.

20. A system for the identification and sorting of recyclable material, the system comprising:

a conveyor belt having a first end opposite a second end, a first portion comprising the first end, a second portion comprising the second end, a middle portion between the first and second portions, and a longitudinal axis extending from the first end to the second end, the conveyor belt having an upper surface and being configured to convey a heterogeneous material stream at a preset rate of travel on the upper surface from the first portion to the second portion, wherein the heterogeneous material stream comprises a mixture of waste and recyclable material;

a hyperspectral identification system capable of receiving spectral and spatial data corresponding to a target recyclable material found within the heterogeneous material stream, the hyperspectral identification system comprising:

a single hyperspectral camera disposed proximate to a light source and capable of receiving a plurality of spectral bands of infrared and visible light corresponding to spectral signatures of desired recyclable materials, wherein the desired recyclable materials include glass, paper, PET plastics, and black plastics, wherein the target recyclable material is one of the desired recyclable materials, the single hyperspectral camera configured to receive a plurality of spectral bands of infrared and visible light corresponding to spectral signatures of the target recyclable material and configured to receive spatial data corresponding to the target recyclable material's position on the conveyor belt, wherein the hyperspectral camera is positioned directly above the second portion and above the upper surface of the conveyor belt;

a computer configured to receive from the hyperspectral identification system information corresponding to the spectral signatures of the target recyclable material and spatial data corresponding to the target recyclable material's position on the conveyor belt, using at least one of that information and data to identify the position of the target recyclable material on the conveyor belt;

an ejector positioned immediately after the second portion of the conveyor belt and in operative communication with the computer, the ejector comprising:

a plurality of jets positioned substantially perpendicular to the longitudinal axis of the conveyor belt and configured to receive one or more signals from the computer to trigger one or more of the jets to move the target recyclable material, wherein the one or more signals correspond to a time delay equal to a distance along the longitudinal axis between a point at which the target recyclable material is identified by the hyperspectral identification system and the one or more of the jets, divided by the preset rate of travel of the conveyor belt; and an ejection plate configured to house the plurality of jets; and a receiving system comprising:

a collection point; and a collection hood positioned above the upper surface of the conveyor belt and proximate the ejector, the collection hood further comprising an evacuation fan configured to provide a current of air to move the target recyclable material to the collection point from which it may be collected.

21. The system according to claim 20, wherein the hyperspectral identification system is configured to collect spectral and spatial information from the recyclable material in the heterogeneous material stream entering the system and to store the spectral and spatial information as stored images, and wherein the computer comprises software configured to compare the stored images to images in a library of images.

22. The system according to claim 20, wherein the target recyclable material is at least one of plastic, glass, and paper.

23. The system according to claim 20, wherein the hyperspectral camera is configured to receive the plurality of spectral bands of infrared and visible light with wavelengths up to at least 1700 nm.

* * * * *